United States Patent
Roehe et al.

(10) Patent No.: US 6,764,508 B1
(45) Date of Patent: Jul. 20, 2004

(54) METHOD AND DEVICE FOR INSERTING IMPLANTS INTO HUMAN ORGANS

(75) Inventors: Oliver Roehe, Ritterhude (DE); Horst Laube, Berlin (DE); Martin Matthaeus, Berlin (DE)

(73) Assignee: co.don AG, Teltow (DE)

(*) Notice: Subject to any disclaimer, the term of this patent is extended or adjusted under 35 U.S.C. 154(b) by 0 days.

(21) Appl. No.: 10/049,703

(22) PCT Filed: Sep. 22, 2000

(86) PCT No.: PCT/DE00/03310
§ 371 (c)(1),
(2), (4) Date: Feb. 14, 2002

(87) PCT Pub. No.: WO01/21111
PCT Pub. Date: Apr. 29, 2001

(30) Foreign Application Priority Data

Sep. 23, 1999 (DE) .......................... 199 45 587

(51) Int. Cl.[7] .................................................. A61F 2/24
(52) U.S. Cl. .................... 623/2.11; 623/23.64; 623/2.38
(58) Field of Search .............................. 623/2.11, 2.38, 623/2.39, 2.4, 2.41, 900

(56) References Cited

U.S. PATENT DOCUMENTS

| | | | | |
|---|---|---|---|---|
| 4,705,516 A | * | 11/1987 | Barone et al. ............. | 623/2.39 |
| 5,406,857 A | * | 4/1995 | Eberhardt et al. ......... | 73/866.4 |
| 5,628,781 A | * | 5/1997 | Williams et al. ........... | 623/1.39 |
| 5,776,188 A | * | 7/1998 | Shepherd et al. .......... | 623/2.38 |
| 5,776,198 A | * | 7/1998 | Rabbe et al. ............. | 623/17.15 |
| 5,823,342 A | * | 10/1998 | Caudillo et al. ............ | 206/438 |
| 5,976,183 A | * | 11/1999 | Ritz .......................... | 623/2.11 |
| 6,074,418 A | * | 6/2000 | Buchanan et al. ......... | 623/2.11 |
| 6,106,550 A | * | 8/2000 | Magovern et al. ......... | 623/2.38 |
| 6,176,877 B1 | * | 1/2001 | Buchanan et al. ......... | 623/2.39 |
| 6,214,407 B1 | | 4/2001 | Laube et al. | |
| 6,241,765 B1 | * | 6/2001 | Griffin et al. .............. | 623/2.38 |

FOREIGN PATENT DOCUMENTS

| | | |
|---|---|---|
| DE | 4316971 | 11/1994 |
| DE | 19834396 | 2/2000 |
| WO | WO99/33414 | 7/1999 |

* cited by examiner

Primary Examiner—Suzette J. Jackson
(74) Attorney, Agent, or Firm—W. F. Fasse; W. G. Fasse

(57) ABSTRACT

In a method for inserting an implant, such as a biological or artificial heart valve into a human organ, first the implant is provided with an adapter element, then a receiver element that is adapted to fit the adapter element is sutured to the recipient organ, and finally the adapter element is connected to the receiver element. The receiver element and the adapter element are each ring-shaped and are provided with matched interengageable threadings. They are connected with one another by relative rotation via a self-locking bayonet lock. Before being connected to the receiver element, the implant together with the adapter element are coated with living cells. Both the receiver element and the adapter element respectively have flanges that include elements for being sutured together with the recipient organ or the implant.

19 Claims, 2 Drawing Sheets

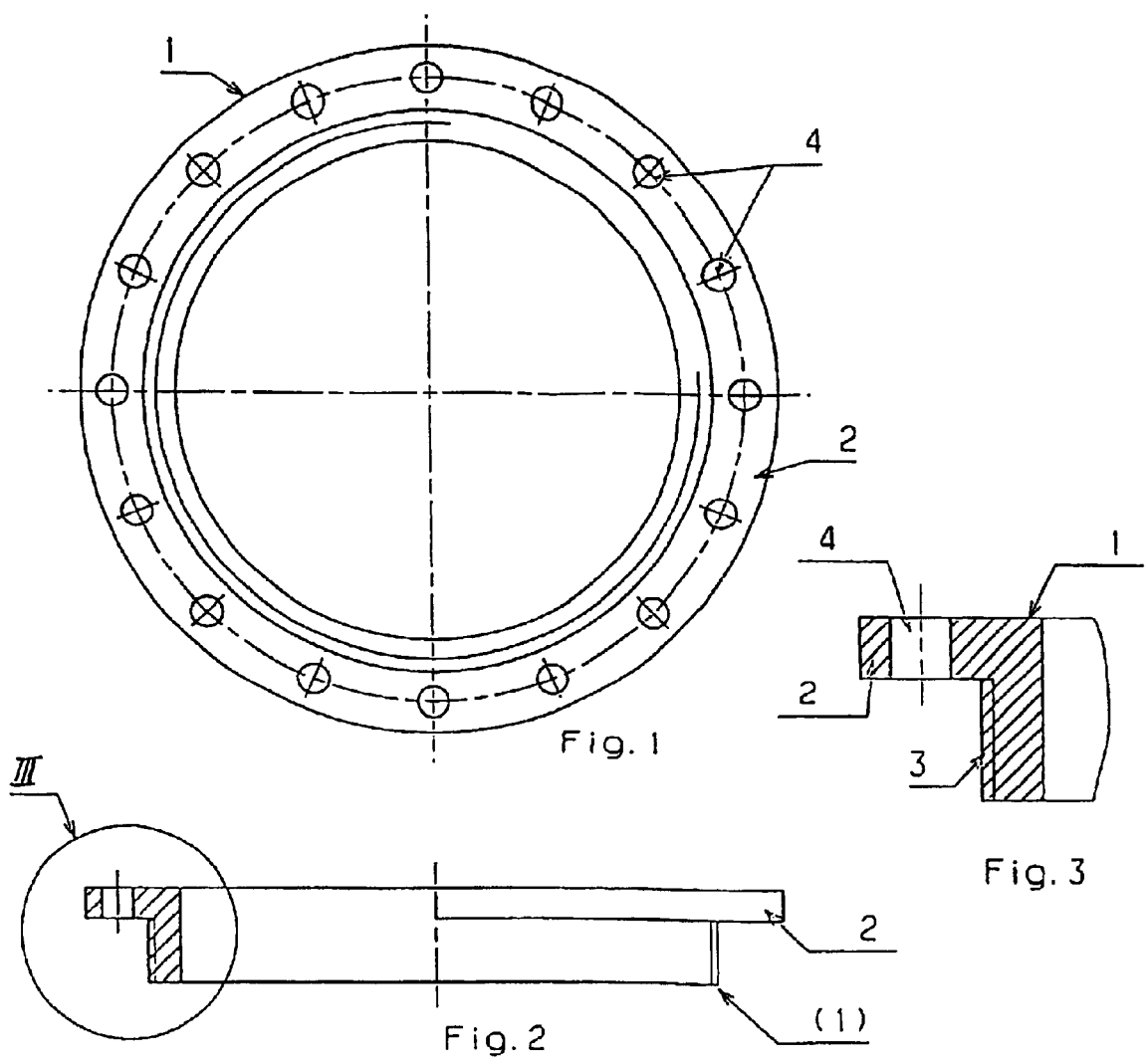

METHOD AND DEVICE FOR INSERTING IMPLANTS INTO HUMAN ORGANS

Literal Translation Of PCT International Application PCT/DE00/03310 as filed on Sep. 22, 2000

FIELD OF THE INVENTION

The invention relates to a method for the insertion of implants into human organs, especially for the installation of biological as well as artificial heart valves, as well as an apparatus for carrying out a method of this kind.

BACKGROUND OF THE INVENTION

In order to prevent, or at least reduce to a minimum, the immune reaction of the human organism with respect to implanted organ parts which are foreign to the body, and in order to prolong the long term durability or service life of special biological implants, it is an already known measure to coat the surfaces of the implants with living cells before the implantation into the human organism. Ideally, homologous cells, i.e. the body's own cells, or cells identical thereto, are concerned in this context. In that regard, the coating of the implants can be carried out in an especially advantageous manner in an apparatus as is described in the German Patent 198 34 396 C1 and corresponding U.S. Pat. No. 6,214,407.

In any event, it is important in this procedure, that the vital cell layer of the thusly prepared organ parts, which are especially biological as well as synthetic or artificial heart valves, is not destroyed by the surgical implantation technique, or are implanted into the human body, in this case into the recipient heart, in the shortest possible operation time after the completed coating, so that the applied cells do not already begin to die off before the successful completion of the transplantation.

SUMMARY OF THE INVENTION

An object of the invention is to develop a method of the above initially described type in such a manner so that it is ensured that artificial or biological organ parts, especially those that have been subjected to a cell coating before the implantation, can be inserted into the recipient organ in a short time and in an irritation-free manner to the extent possible. Moreover, it is an object of the invention, to provide an apparatus for carrying out a method of this type.

The invention achieves the first object by a method in which the implant is provided with an adapter element, a receiver element adapted or matched to the adapter element is sutured together with the recipient organ, and the adapter element is connected with the receiver element. The further object is achieved according to the invention by an apparatus, in which both the receiver element as well as the adapter element are embodied with a ring shape and are respectively provided with a flange-like shoulder or projection.

In an advantageous further development of the invention, it is provided in this context, that the connection of adapter element and receiver element is achieved via a fastener, that is embodied as a bayonet lock and essentially only requires a rotation or turning. Moreover, this fastener is equipped with self-locking guide elements in an advantageous embodiment of the invention.

Therewith the invention has the advantage, that the elements that are to be connected with one another cannot be loosened or released from one another in an automatic or self-acting manner, also in connection with a pulsating internal pressure, as it exists in connection with the heart. By means of elastic seal edges, a sufficient seal to the inside and to the outside is ensured simultaneously. On the other hand, a loosening or releasing of the connection is also still possible after several years of installed use, as the case may be, with the aid of a specially fitted disassembly tool. Thereby it is possible to fabricate the adapter element as well as the receiver element of a sterilizable body-compatible synthetic material. Finally, the adapter element provided in the apparatus according to the invention has the advantage that it can, without problems, be coated with living cells, together with the organ part that is to be implanted, preferably a biological as well as artificial heart valve, in the apparatus described in the German Patent 198 34 396 C1 and the corresponding U.S. Pat. No. 6,214,407

BRIEF DESCRIPTION OF THE DRAWING

In the following, the invention shall be described in further detail in connection with an example embodiment illustrated as a general principle in the drawing. Therein:

FIG. 1 shows a top plan view onto a receiver element,

FIG. 2 shows, the element according to FIG. 1 in a partially sectioned side illustration, FIG. 3 shows an enlarged detail illustration III of the arrangement according to FIG. 2.

DETAILED DESCRIPTION OF A PREFERRED EXAMPLE OF THE INVENTION

Figure 4:
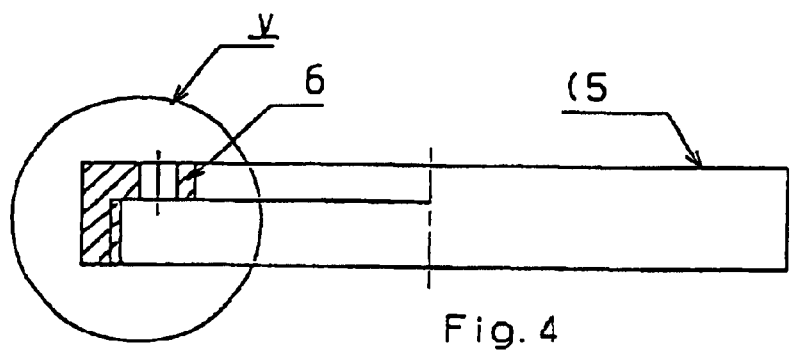
FIG. 4 shows a partially sectioned side illustration of an adapter element.

The receiver element 1 illustrated in the FIGS. 1 to 3 essentially consists of a ring that is provided with a flange-like shoulder or projection 2 and that has a threading 3 on its outer surface. In the presently illustrated example embodiment, in which the receiver element 1 serves for the implantation of an artificial heart valve, this ring, with an outer diameter of 29 mm and a width of about 3 mm, comprises a four-fold sharp V-thread with a pitch of 8 mm and a web width of 1 mm. In the presently illustrated example embodiment, the web height amounts to 0.5 mm. The flange 2 is provided with a set of bored through holes 4, which comprise a diameter of 0.4 mm in the presently illustrated example embodiment, and which serve for the suturing with the recipient organ, in this case the recipient heart.

Figure 5:
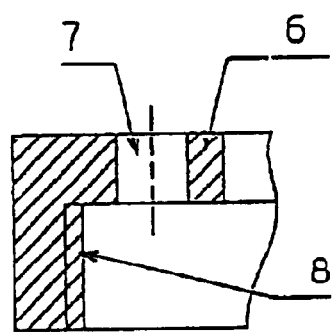
FIG. 5 shows an enlarged detail illustration V of the arrangement according to FIG. 4.
Figure 6:
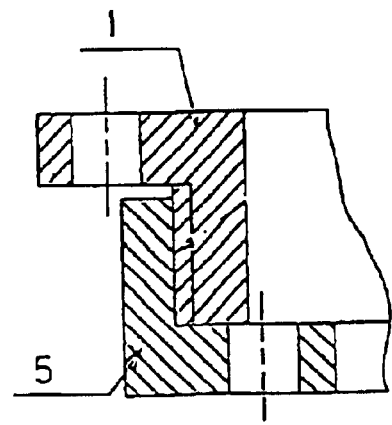
FIG. 6 shows an enlarged detail illustration of the threading in the screwed-together position

The adapter element 5 illustrated in the FIGS. 4 and 5 is similarly embodied as a ring with a flange-like shoulder or projection 6, whereby the flange is again provided with bored holes 7. In its interior, the adapter element 5 is provided with an internal threading 8, of which the dimensions are adapted or matched to the external threading of the receiver element 1. Both elements 1 and 5 consist of a sterilizable body-compatible synthetic or plastic.

In connection with the insertion of an artificial heart valve, before the actual operation, this valve is first connected with the adapter element 5, in this case being sutured together, and together with the adapter element is coated on the surface with living cells in an apparatus especially embodied for this purpose. Then, for beginning the transplantation operation, first the receiver element 1 is sutured into the heart, and in the following step the coated combination of heart valve and adapter element 5 is inserted into the receiver element 1, and both components are mechanically securely connected with one another by relative rotation or turning by about 30 angular degrees.

What is claimed is:

1. A system for inserting an implant into a human organ, comprising:
   an implant;
   an adapter element comprising a ring-shaped adapter body and an annular adapter flange projecting radially from said adapter body;
   a first suture connecting said adapter flange to said implant;
   a receiver element comprising a ring-shaped receiver body and an annular receiver flange that projects radially from said receiver body and is adapted to be connected to a human organ; and
   a second suture adapted to connect said receiver flange to the human organ;
   wherein said adapter body has a first threading, said receiver body has a second threading, and said first and second threadings are configured and adapted to be threadingly engaged with each other to releasably connect said adapter body with said receiver body.

2. The system according to claim 1, further comprising an integral coating layer of living cells continuously integrally covering a surface of said implant and an adjoining surface of said adapter element.

3. A method of inserting an implant into a human organ, comprising the steps:
   a) providing an implant;
   b) connecting said implant to an adapter element;
   c) suturing a receiver element to a human organ; and
   d) connecting said adapter element, with said implant connected thereto, to said receiver element by rotating said adapter element relative to said receiver element.

4. The method according to claim 3, wherein said receiver element and said adapter element respectively include first and second threadings, and said rotating of said adapter element relative to said receiver element comprises engaging and screwing together said first and second threadings.

5. The method according to claim 3, further comprising an additional step, performed after said step b) and before said step d), of coating a surface of said adapter element and of said implant connected to said adapter element with a coating layer of living cells.

6. A system for inserting an implant into a human organ comprising:
   an adapter element comprising a ring-shaped adapter body and an annular adapter flange projecting from said adapter body; and
   a receiver element comprising a ring-shaped receiver body and an annular receiver flange projecting from said a receiver body;
   wherein said adapter flange is adapted to be connected to an implant, said receiver flange is adapted to be connected to a human organ, said adapter body has a first threading, said receiver body has a second threading, and said first and second threadings are configured and adapted to be threadingly engaged with each other to connect said adapter body with said receiver body.

7. The system according to claim 6, wherein said second threading is an external threading on said receiver body.

8. The system according to claim 7, wherein said first threading is an internal threading in said adapter body.

9. The system according to claim 8, wherein said internal threading and said external threading comprise lock threads.

10. The system according to claim 8, wherein said receiver flange projects radially outwardly from said receiver body and said adapter flange projects radially inwardly from said adapter body.

11. The system according to claim 6, wherein said receiver flange projects radially outwardly from said receiver body and said adapter flange projects radially inwardly from said adapter body.

12. The system according to claim 6, wherein said adapter flange has first elements adapted to receive a suture to connect said adapter flange to the implant, and said receiver flange has second elements adapted to receive a suture to connect said receiver flange to the human organ.

13. The system according to claim 12, wherein said first elements are first throughholes in said adapter flange and said second elements are second throughholes in said receiver flange.

14. The system according to claim 6, further comprising said implant, a first suture connecting said adapter flange to said implant, and a second suture connecting said receiver flange to the human organ.

15. The system according to clam 14, further comprising a coating layer of living cells covering a surface of said implant and a surface of said adapter element.

16. The system according to claim 14, wherein said implant is a biological heart valve.

17. The system according to claim 14, wherein said implant is an artificial heart valve.

18. The system according to claim 6, wherein said adapter element is a one-piece plastic adapter element integrally including said adapter body and said adapter flange, and said receiver element is a one-piece plastic receiver element integrally including said receiver body and said receiver flange.

19. A system for inserting a biological heart valve as an implant into a human heart comprising:
   a biological heart valve;
   an adapter element comprising a ring-shaped adapter body and an annular adapter flange projecting from said adapter body;
   a first suture connecting said biological heart valve to said adapter flange;
   a receiver element comprising a ring-shaped receiver body and an annular receiver flange projecting from said receiver body; and
   a second suture connecting said receiver flange to a human heart;
   wherein said adapter body and said receiver body are adapted to be connected to each other.

* * * * *

UNITED STATES PATENT AND TRADEMARK OFFICE
CERTIFICATE OF CORRECTION

PATENT NO. : 6,764,508 B1
DATED : July 20, 2004
INVENTOR(S) : Roehe et al.

It is certified that error appears in the above-identified patent and that said Letters Patent is hereby corrected as shown below:

Title page,
Item [87], PCT Pub. Date, after "Date:" replace "Apr. 29, 2001" by -- March 29, 2001 --.

Column 1,
Lines 4 and 5, delete these lines.

Signed and Sealed this

Twenty-seventh Day of September, 2005

JON W. DUDAS
*Director of the United States Patent and Trademark Office*